United States Patent
Hoy

[11] 3,940,448
[45] Feb. 24, 1976

[54] FORMALDEHYDE-DIAROMATIC ETHER REACTION PRODUCTS

[75] Inventor: Edgar F. Hoy, Midland, Mich.

[73] Assignee: The Dow Chemical Company, Midland, Mich.

[22] Filed: Feb. 25, 1974

[21] Appl. No.: 445,514

[52] U.S. Cl. ...... 260/609 F; 260/611 A; 260/613 R; 260/47 R
[51] Int. Cl.² ........................................ C07C 149/32
[58] Field of Search .......... 260/611 A, 613 R, 47 R, 260/609 F

[56] References Cited
UNITED STATES PATENTS

| | | | |
|---|---|---|---|
| 3,052,640 | 9/1962 | Martin | 260/611 A |
| 3,274,157 | 9/1966 | Doedens | 260/47 R |
| 3,303,167 | 2/1967 | Kakiuchi et al. | 260/611 A |
| 3,342,873 | 9/1967 | Doedens | 260/47 R |
| 3,686,320 | 8/1972 | Fitzmaurice et al. | 260/613 R |

FOREIGN PATENTS OR APPLICATIONS

942,057 11/1963 United Kingdom ............. 260/611 A

OTHER PUBLICATIONS

Die Makromolekulore Chemie 97 (1966) pp. 163-173.

Primary Examiner—Lewis Gotts
Assistant Examiner—D. R. Phillips
Attorney, Agent, or Firm—Glwynn R. Baker

[57] ABSTRACT

A condensation product being a co-generic mixture of products having the formulae

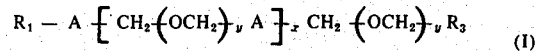

(I)

wherein each A is an independently selected aromatic radical having the formula

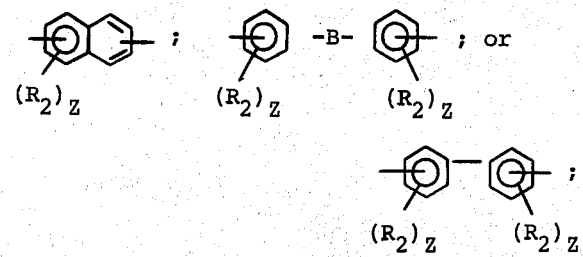

each $R_1$ represents an independently selected radical from the group consisting of hydrogen, $-CH_2-(OCH_2)_y-R_3$; each $R_2$ represents an independently selected radical consisting of $R_1$, halogen or an alkyl group of 1 to 10 carbon atoms; $R_3$ represents a radical selected from the group consisting of hydrogen, methoxy, ethoxy, propoxy or $-A-H$ when $y$ is 1 or greater than 1 and methoxy, ethoxy, propoxy and $-A-H$ when $y$ is 0; $x$ represents an integer from 0 to 60; $y$ represents an integer from 0 to 4; $z$ represents an integer from 0 to 2; and, B represents oxygen or sulfur. It is to be understood that unreacted aromatic HAH may be present in amounts up to 50% by weight of the total condensation product.

4 Claims, No Drawings

FORMALDEHYDE-DIAROMATIC ETHER REACTION PRODUCTS

BACKGROUND OF THE INVENTION

This invention relates to reaction products of formaldehyde, with diaryl compounds such as naphthalene, alone and in combination with diphenyl oxide, and to a process for their preparation.

It is known from Makromolekulare Chemie 97:163 (1966) and 107:196 (1967); British Pat. No. 942,057; and Ser. No. 236,472 filed March 20, 1972 that resins can be prepared from formaldehyde and diphenyl oxide. However, the resins do not have methoxymethyl substituents.

It is also known from J. Research 17, B:14-20 (1939) by R. Monske and A. Ledinghorn, U.S. Pat. Nos. 3,342,873 and 3,274,157 that alkyloxymethyl diphenyl ethers and naphthalene ethers can be prepared by chloromethylating diphenyl ether or naphthalene and then etherifying with lower alcohols. The present route of directly preparing methoxymethyl derivatives is advantageous as it avoids the intermediacy of chloromethyl ethers.

SUMMARY OF THE INVENTION

The present invention is a mixture of products having the formulae $$R_1 - A + CH_2 + OCH_2 +_y A +_x CH_2 + OCH_2 +_y R_3 \quad (I)$$

wherein each A is an independently selected aromatic radical having the formula

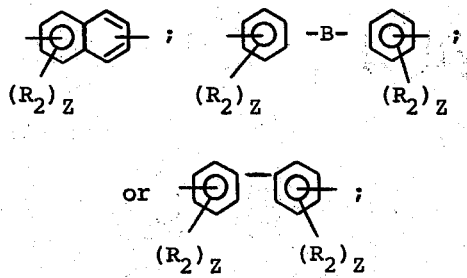

each $R_1$ represents an independently selected radical from the group consisting of hydrogen, $+CH_2+OCH_2-_yR_3$; each $R_2$ represents an independently selected radical consisting of $R_1$, halogen or an alkyl group of 1 to 10 carbon atoms; $R_3$ represents a radical selected from the group consisting of hydrogen, methoxy, ethoxy, propoxy or —A—H when $y$ is 1 or greater than 1 and methoxy, ethoxy, propoxy and —A—H when $y$ is 0; $x$ represents an integer from 0 to 60; $y$ represents an integer from 0 to 4; $z$ represents an integer from 0 to 2; and, B represents oxygen or sulfur. It is to be understood that unreacted aromatic HAH may be present in amounts up to 50% by weight of the total condensation product.

The process of making the reaction (condensation) products comprises heating to a temperature in the range from about 50° to about 250°C a mixture of A. a diaryl compound selected from naphthalene, its alkylated and/or halogenated derivatives alone or in combination with diphenyl oxide, diphenyl sulfide, biphenyl, their alkylated derivatives, their halogenated derivatives, or mixtures thereof, B. formaldehyde, C. water, and D. an aliphatic hydroxy hydrocarbon compound having 1-12 carbon atoms, 0-4 ether oxygens, not more than 4 carbon atoms between ether oxygens and at least one free hydroxyl group, e.g. methanol, 2-ethylhexanol, methyl ether of ethylene glycol, etc.

in the presence of a catalytic amount of a strong acid catalyst wherein the amount of formaldehyde used ranges from about 1 to about 3 moles per mole of diaryl compound, the amount of water ranges from about 0.01 to about 2 moles per mole of diaryl compound and the amount of hydroxy hydrocarbon compound ranges from about 0.3 to about 10 moles per mole of diaryl compound.

The reaction products are useful in that they can be heated with strong acids and crosslinked to form films and to encapsulate electrical components. The reaction products are useful per se as nontoxic dielectric fluids for capacitors and the like.

DETAILED DESCRIPTION

The reaction products (condensation products) of this invention are obtained by reacting naphthalene, alone or in combination with diphenyl ether (diphenyl oxide), diphenyl sulfide and biphenyl with formaldehyde and appropriate hydroxy containing compounds. Reaction products can also be prepared from the alkylated derivatives of the foregoing wherein one or both aromatic rings are substituted by one or two alkyl groups of 1-10 carbon atoms each.

If desired, the naphthalene and diaromatic ethers can be halogenated in one or both rings with fluorine, chlorine, bromine, or iodine groups. Mixtures of the foregoing are also useful in this invention.

The naphthalene alone or in combination with the diaromatic ethers is mixed and reacted with about 1 to about 3 moles of formaldehyde based on the total aromatic present at a temperature range from about 50° to about 250°C in the presence of about 0.01 to about 2 moles of water per mole of aromatic hydrocarbon and in the presence of about 0.3 to about 10 moles of an aliphatic hydroxy $C_{1-12}$ hydrocarbon compound having 0–4 ether oxygens, not more than 4 carbon atoms between ether oxygens and at least one free hydroxyl group.

The presence of water in the ranges recited above is essential to this invention since the use of amounts below this range results in very low yields of the desired reaction product while amounts greater than this amount result in greatly increased reaction times.

The above reaction proceeds readily in the presence of a catalytic amount of a strong acid catalyst. For the purposes of this invention a catalytic amount is defined as about 1 to about 25 mol percent of the strong acid based on the aromatic hydrocarbon.

Examples of strong acid catalysts are sulfuric, phosphoric, p-toluene sulfonic acid, perchloric, diphenyl oxide, sulfonic acid and the like.

A commercial mixture of formaldehyde, methanol and water sold under the trade name Methyl Formcel is a convenient source of the above formaldehyde reactant.

Examples of the above aliphatic hydroxy $C_{1-12}$ hydrocarbon compounds are: monohydric alcohols of 1–12 carbons such as methanol, ethanol, propanol, butanol, 2-ethyl hexanol and the like; glycols of 2–4 carbons such as ethylene glycol, 1,3-propylene glycol, 1,2-propylene glycol and butane 1,4-diol; polyglycols of 4–12 total carbons such as diethylene glycol, triethylene glycol, dipropylene glycol, tripropylene glycol, and the like; monoalkyl ethers of glycols of 3–12 total carbons such as ethylene glycol monomethyl ether, ethylene glycol monoethyl ether, 1,2-propylene glycol monomethyl ether, ethylene glycol monobutyl ether, and the like; and monoalkylethers of polyglycols of 5–12 total carbons such as diethylene glycol monomethyl ether, diethylene glycol monoethyl ether, diethyleneglycol monobutyl ether, and the like.

The following examples are presented to illustrate but not limit the invention.

EXAMPLE 1

An acid resistant pressure vessel equipped with paddle stirrer and thermowell was charged with 256 g. naphthalene, 64 g. of 91% paraformaldehyde, 36 g. water, 128 g. methanol and 42 g. 98% sulfuric acid. The mixture was heated with stirring at 143° for 4 hours and cooled. The organic layer was diluted with 300 ml. methylene chloride. This organic layer was washed with dilute (10%) aqueous caustic and dried. Analysis by vapor phase chromatography showed ca. 65% of the naphthalene had been converted to product. The average molecular weight as determined by gel permeation chromatography was approximately 210 ranging from 128 to 350 with major peaks at 128, 165 and 270. Following distillation of the unreacted naphthalene the residue weighed 187 g. Analysis by NMR showed the following relative areas:

| aromatic hydrogens | 102 |
| --- | --- |
| $(CH_2O)_x$ hydrogens | 8 |
| bis(naphthyl)methane | 12 |
| $(OCH_3)_x$ hydrogens | 12 |

EXAMPLE 2

An acid resistant (Hastelloy C) pressure vessel with a paddle stirrer and thermowell was charged with 228 g. diphenyl oxide, 86 g. of naphthalene, 64 g. of 91% paraformaldehyde, 135 g. of methanol, 40 g. 96% sulfuric acid and 36 g. of water. The mixture was heated with stirring at 148°C. for 3 hours and then cooled. The top organic phase was decanted and vacuum dried to remove the unreacted methanol, formaldehyde and water. An analysis by vapor phase chromatography showed that ~60% of the diphenyl oxide had reacted and ~50% of the naphthalene had been converted. A gel permeation analysis showed a molecular weight range from 128 to 900 units with an average molecular weight of 290. The crude organic layer was vacuum distilled with 39 g. of naphthalene and 57 g. of diphenyloxide being recovered. The weight of the final product was 148 g. with an average molecular weight of 300. An analysis by NMR showed the following relative areas.

| aromatic hydrogens | 95 |
| --- | --- |
| $(CH_2O)_x$ | 27 |
| bis(phenoxyphenyl)methane | 3 |
| bis(naphthyl)methane | 4 |
| $OCH_3$ | 30 |

EXAMPLE 3

An acid resistant (Hastelloy C) pressure vessel with a paddle stirrer and a thermowell was charged with 119 g. of diphenyl oxide, 166 g. of naphthalene, 64 g. of 91% paraformaldehyde, 128 g. methanol, 40 g. of sulfuric acid, 36 g. of water. The mixture was heated to 148°C. for 4 hours and cooled. The organic phase was decanted and diluted with 100 g. of methylene chloride. The resulting solution was washed twice with 100 g of water and then vacuum dried. An analysis by vapor phase chromatography showed ≈50% of the naphthalene and 60% of the diphenyl oxide had been converted to product. The gel permeation showed an average molecular weight of 270. An NMR analysis showed the following relative areas.

| aromatic hydrogen | 75 |
| --- | --- |
| $(CH_2O)$ | 10 |
| bis(phenoxyphenyl)methane | 5 |
| bis(naphthyl)methane | 2 |
| $OCH_3$ | 10 |

There was 114 g. isolated after vacuum distillation of the unreacted diphenyl oxide and naphthalene.

We claim:

1. A cogeneric liquid formaldehyde aromatic ether reaction product having the formulae $$R_1 - A + CH_2 + OCH_2 + _yA +_x CH_2 + OCH_2 +_y R_3 \quad (I)$$

wherein each A is an independently selected aromatic radical having the formula

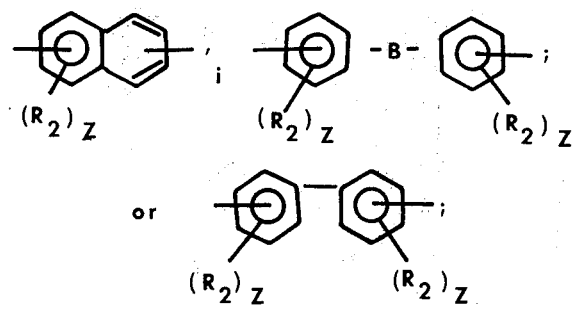

each $R_1$ represents an independently selected radical from the group consisting of hydrogen, $+CH_2+OCH_2-_yR_3$ each $R_2$ represents an independently selected radical consisting of $R_1$, halogen or an alkyl group of 1 to 10 carbon atoms; $R_3$ represents a radical selected from the group consisting of hydrogen, methoxy, ethoxy, propoxy or —A—H when y is 1 or greater than 1 and methoxy, ethoxy, propoxy and —A—H when y is 0; x represents an integer from 0 to 60; y represents an integer from 0 to 4; z represents an integer from 0 to 2; and, B represents oxygen or sulfur, which may contain unreacted amounts up to 50% by weight of unreacted aromatic HAH of the total condensation product.

2. A process for preparing a liquid formaldehydediaromatic ether reaction product which comprises heating to a temperature in the range from about 50° to about 250° a mixture of
   A. an aromatic compound selected from naphthalene alone or in combination with diphenyl oxide, diphenyl sulfide, biphenyl, their alkylated and/or halogenated derivatives, or mixtures thereof,
   B. formaldehyde,
   C. water, and D. an aliphatic hydroxy hydrocarbon compound having 0–4 ether oxygens, and not more than 4 carbon atoms between ether oxygens and at least one free hydroxyl group, in the presence of a catalytic amount of a strong acid catalyst wherein the amount of formaldehyde used ranges from about 1 to about 3 moles per mole of diaryl compound, the amount of water ranges from about 0.01 to about 2 moles per mole of diaryl compound and the amount of hydroxy hydrocarbon compound ranges from about 0.3 to about 10 moles per mole of diaryl compound.

3. The process as set forth in claim 2 wherein the hydroxy hydrocarbon compound is selected from aliphatic monohydric alcohols of 1–12 carbons, glycols of 2–4 carbons, polyglycols of 4–12 carbons, monoalkyl ethers of polyglycols of 5–12 carbons, and monoalkyl ethers of glycols of 3–12 carbons.

4. A cogeneric liquid formaldehyde aromatic ether reaction product having the formulae

  (I)

wherein each A is an independently selected aromatic radical having the formula

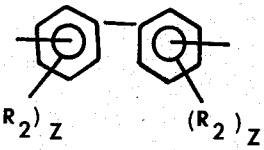

each $R_1$ represents an independently selected radical from the group consisting of hydrogen, $-CH_2-OCH_2-_yR_3$; each $R_2$ represents an independently selected radical consisting of $R_1$, halogen or an alkyl group of 1 to 10 carbon atoms, $R_3$ represents a radical selected from the group consisting of hydrogen, methoxy, ethoxy, propoxy or $-A-H$ when $y$ is 1 or greater than 1 and methoxy, ethoxy, propoxy and $-A-H$ when $y$ is 0; $x$ represents an integer from 0 to 60; $y$ represents an integer from 0 to 4; $Z$ represents an integer from 0 to 2; and, B represents oxygen or sulfur, which may contain unreacted amounts up to 50% by weight of unreacted aromatic HAH of the total condensation product.

* * * * *

UNITED STATES PATENT AND TRADEMARK OFFICE
CERTIFICATE OF CORRECTION

PATENT NO. : 3,940,448
DATED : February 24, 1976
INVENTOR(S) : Edgar F. Hoy

It is certified that error appears in the above-identified patent and that said Letters Patent are hereby corrected as shown below:

Col. 4, line 12, delete "≈" and insert -- ≃ --

Col. 4, Claim 1, line 35, after the first formula, delete the semicolon ";" and insert -- alone or in combination with --

Signed and Sealed this eighteenth Day of May 1976

[SEAL]

Attest:

RUTH C. MASON
Attesting Officer

C. MARSHALL DANN
Commissioner of Patents and Trademarks